United States Patent [19]

Dahlberg et al.

[11] 4,287,303
[45] Sep. 1, 1981

[54] PRODUCTION OF ETHANOL

[75] Inventors: Bengt I. Dahlberg, Uttran; Lars K. J. Ehnström, Tullinge, both of Sweden; Carroll R. Keim, Stamford, Conn.

[73] Assignee: Alfa-Laval AB, Tumba, Sweden

[21] Appl. No.: 93,068

[22] Filed: Nov. 13, 1979

[51] Int. Cl.$^3$ ............................................. C12P 7/14
[52] U.S. Cl. .................................. 435/162; 435/163; 435/165
[58] Field of Search ............... 435/165, 162, 161, 163; 426/492, 493, 14, 16, 11, 62

[56] References Cited

U.S. PATENT DOCUMENTS

| 385,625 | 7/1888 | Horne | 435/165 |
|---|---|---|---|
| 504,074 | 8/1893 | Bradley et al. | 435/165 |
| 963,275 | 7/1910 | Chute | 435/162 |

FOREIGN PATENT DOCUMENTS 2013716  8/1979  United Kingdom ..................... 435/162

Primary Examiner—R. B. Penland
Attorney, Agent, or Firm—Cyrus S. Hapgood

[57] ABSTRACT

In the production of ethanol in plants, comprising a fermenter, a centrifugal separator for the recirculation of the yeast to the fermenter and a plant for the separation of a yeast-free flow, coming from the centrifugal separator, into one flow, rich in ethanol, and into one residual flow, the substrate, that is fed to the fermenter must be rid of solid substance, like fibres etc. In the separation of such solid substance a certain amount of substrate has been lost according to the methods utilized hitherto, or an unnecessarily high consumption of water and energy has occurred. According to the invention the solid substance, which is separated from the raw material flow, is washed, preferably countercurrently with said residual flow, which in turn, enriched in substrate, is fed to the fermenter. If a distillative method is used for said separation the residual flow is called slop.

4 Claims, 3 Drawing Figures

PRODUCTION OF ETHANOL

The present invention relates to a method for the production of ethanol, from a raw material flow, consisting of a carbohydrate-containing substrate, mixed with cellulose-containing fibres and/or other nonfermentable, solid material, said raw material flow being separated into one flow rich in solid substance and one substrate flow, free from solid substance, which last flow is fermented in one or several fermenters, a flow of fermentation liquor being separated by centrifugal separation, into at least one yeast concentrate flow and one yeast-free flow, of which the yeast concentrate flow is recirculated to the fermenter, while the yeast-free flow is separated into one flow, enriched in ethanol, and one residual flow, of which at least part is recirculated to the fermenter.

Ethanol can be manufactured from several types of raw materials of vegetable origin. These raw materials all contain, or are brought to contain some fermentable carbohydrate, dissolved in water to a more or less high concentration. Depending on the processes, which the raw materials have been subject to, in order to reach at least a certain content of fermentable carbohydrates, such as enzymatic or acid hydrolysis of starch or lignine-containing cellulose raw materials, the substrate, which shall be fermented into ethanol, is more or less mixed with nonfermentable solid matter like cellulose fibres, hulls, lignine etc.

When conceiving fermentation processes for the production of ethanol it is aimed at minimizing the energy demand and the water consumption, and increasing the sugar yield as far as possible.

A process, which meets these demands as far as the raw material is not too much contaminated by fibres, hulls, etc. is described in the Swedish patent application No. 7801133-5, which is concerned with a method for the production of a volatile organic compound, in particular ethanol, by continuous fermentation of a carbohydrate-containing substrate in a fermenter, wherein the characterizing feature is, that a flow of fermentation liquor is separated, by centrifugal separation, into at least one yeast concentrate flow and one yeast-free flow, of which the yeast concentrate flow is recirculated to the fermenter, while the yeast-free flow is separated into one flow, enriched in volatile organic compound, which is discharged, and a residual flow, of which at least part is recirculated to the fermenter.

If the raw material contains fibres, these must be removed before the raw material flow is fed to the fermenter, in such a process. Otherwise it would be impossible to perferom the recirculation of yeast without a simultaneous recirculation of said solid matter. For this reason, the raw material flow fed is usually separated into one substrate flow, which is fed to the fermenter, and one flow, rich in solid substance, by centrifugal separation, said last flow being washed with water, which after washing is enriched with substrate, adhering to the solid substance, and is fed to the fermenter. It is true that such a mode of operation would make possible the performance of the method according to the Swedish Patent Application No. 7801133-5, but it would mean an increased, nondesirable consumption of water and energy.

It is the object of the present invention to create a method of the type mentioned by way of introduction, in which the energy demand and the water consumption is minimized, while the sugar yield is as high as possible.

According to the present invention this problem is solved by bringing the flow, rich in solid substance, into contact with at least part of the residual flow, the mixture thus obtained being separated partly into a flow of solid substance, from which remaining substrate has substantially been removed, and partly into one flow, enriched in substrate, which flow is recirculated to the fermenter.

In one suitable embodiment of the method according to the invention, said mixture is separated by at least one separation means in the form of a sieve means, a flow rich in solid matter being fed to said sieve means together with at least part of said residual flow and separated partly into one solid phase fraction, which is prevented in a way known per se to pass the sieve means without forming a filtering layer on same, and partly into one liquid fraction, enriched in substrate, which fraction is brought to pass said sieves means, and is recirculated to the fermenter.

Said mixture can also be separated by at least one centrifugal separator provided with a rotor, journalled horizontally in bearings and a conveying screw, arranged coaxially within the rotor for discharge of separated heavy phase into one solid substance fraction, which forms heavy phase, and into one liquid fraction, enriched in substrate, which is recirculated to the fermenter.

Vacuum sieves can also be used for the separation into solid phase fraction and substrate-enriched liquid fraction.

It is especially advantageous to bring said flow, rich in solid substance, into contact with at least part of the residual flow by providing several separation means in series, the flow, rich in solid substance and at least part of the residual flow being brought to move countercurrently.

Such countercurrent washing of substrate from the flow, rich in solid substance, can also be performed in different types of extractors, for instance in the form of columns, provided with so called extraction trays.

In one especially suitable embodiment of the method according to the invention the yeast-free flow is separated by a distillative method into one flow enriched in ethanol and one residual flow, so called slop, which is thus utilized for transferring the substrate, that is adhering to the solid substance, to the fermenter.

Considering the efficiency of the transfer of the substrate, adhering to the solid substance to the fermenter, the concentration of the fermentable substance in the slop shall be much lower than that in the raw material flow fed.

The invention shall now be described more in detail, reference being made to the enclosed three figures, of which FIG. 1 shows, schematically, a flow sheet of a plant for the performance of the method according to the Swedish Patent Application No. 7801133-5;

Figure 1:
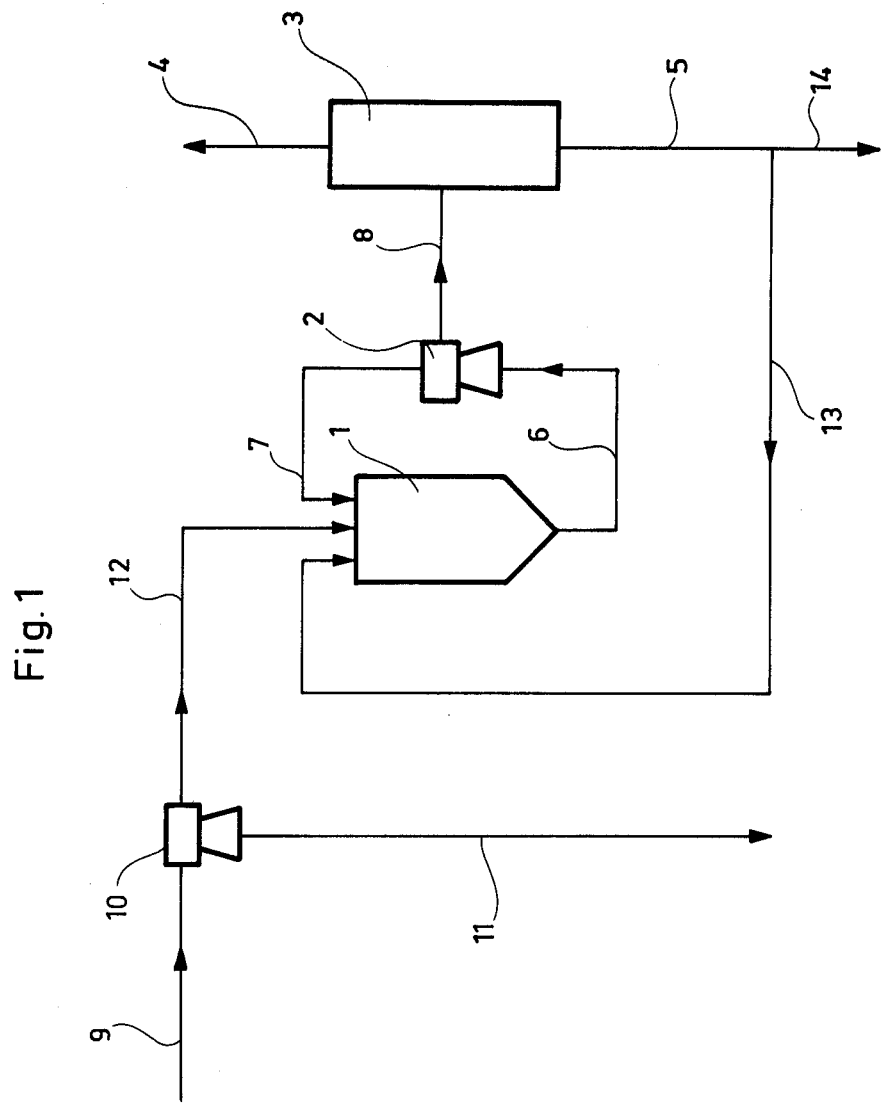

In all figures 1 refers to one (or a plurality of) fermenter, 2 to a centrifugal separator for the recirculation of yeast to same and 3 to a plant for the separation of a yeast-free flow into a flow enriched in ethanol and one residual flow, exhausted from ethanol but containing a certain amount of fermentable viz. nonfermentable material. In the examples shown plant 3 is assumed to be a simple distillation plant, and the residual flow is in the following referred to as "slop".

From the distillation plant 3 there is discharged an enriched ethanol flow through a pipe 4 and a slop flow through a pipe 5. A flow of fermentation liquor is taken through a pipe 6 to centrifugal separator 2, while a separated yeast flow is recirculated via a pipe 7 to the fermenter and a yeast-free flow containing ethanol is fed via a pipe 8 to distillation plant 3. In all three plants shown a raw material flow is fed through a pipe 9.

The plant disclosed in FIG. 1 comprises a centrifugal separator 10, by the aid of which the raw material flow fed is rid of any fibres and other solid matter, which are discharged through a pipe 11, while the substrate flow is fed to the fermenter through a pipe 12. At least part of the slop from distillation plant 3 is recirculated to the fermenter through a pipe 13, while a certain amount of the slop is discharged from the plant through a pipe 14.

Figure 2:
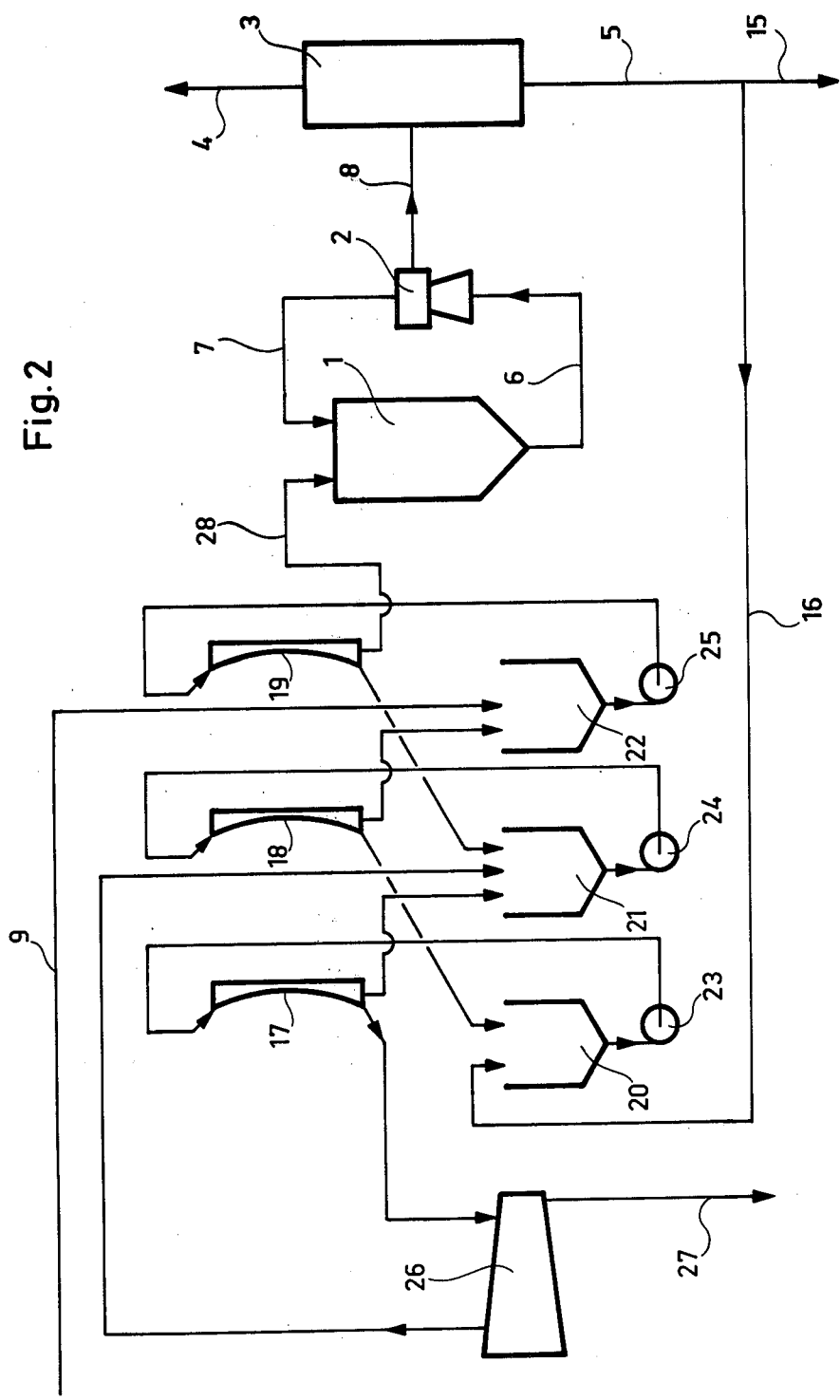
FIG. 2 shows, schematically, a flow sheet of a plant for the performance of the method according to the present invention, three bow-sieves, coupled in series, and a centrifugal separator with horizontal rotor and a coaxial conveying screw for recovery of substrate from flow, rich in solid substande, being used.

In the embodiment of a plant for the performance of the method according to the invention disclosed in FIG. 2, part of the slop is discharged through a pipe 15. The remaining part of the slop flow is fed, via a pipe 16, to a unit for efficient separation of the incoming raw material flow into one solid-substance flow, substantially free from substrate, and one substrate flow. This unit consists of three bow sieves 7, 18 and 19, three mixing tanks 20, 21 and 22 with pumps 23, 24 and 25 connected thereto. There is also a centrifugal separator 26 in the unit. The former is of a type, comprising a rotor, horizontally journalled in bearings, with a conveyor screw provided coaxially within the rotor for discharge of separated heavy phase.

The centrifugal separator and the bow sieves are coupled in series, and the raw material flow, fed through pipe 9 streams countercurrently to the slop flow, fed through pipe 16. The solid substance, which is washed out, is brought to a relatively high dry solids content in centrifugal separator 26 and leaves the plant for further treatment, like drying, through a pipe 27. The substrate flow, rid of fibres etc, is fed to the fermenter through a pipe 28. The line design is disclosed more in detail in the figure. It must be observed, that many different flow sheets are possible. The unit shown is considered to be efficient and economical in operation.

Figure 3:
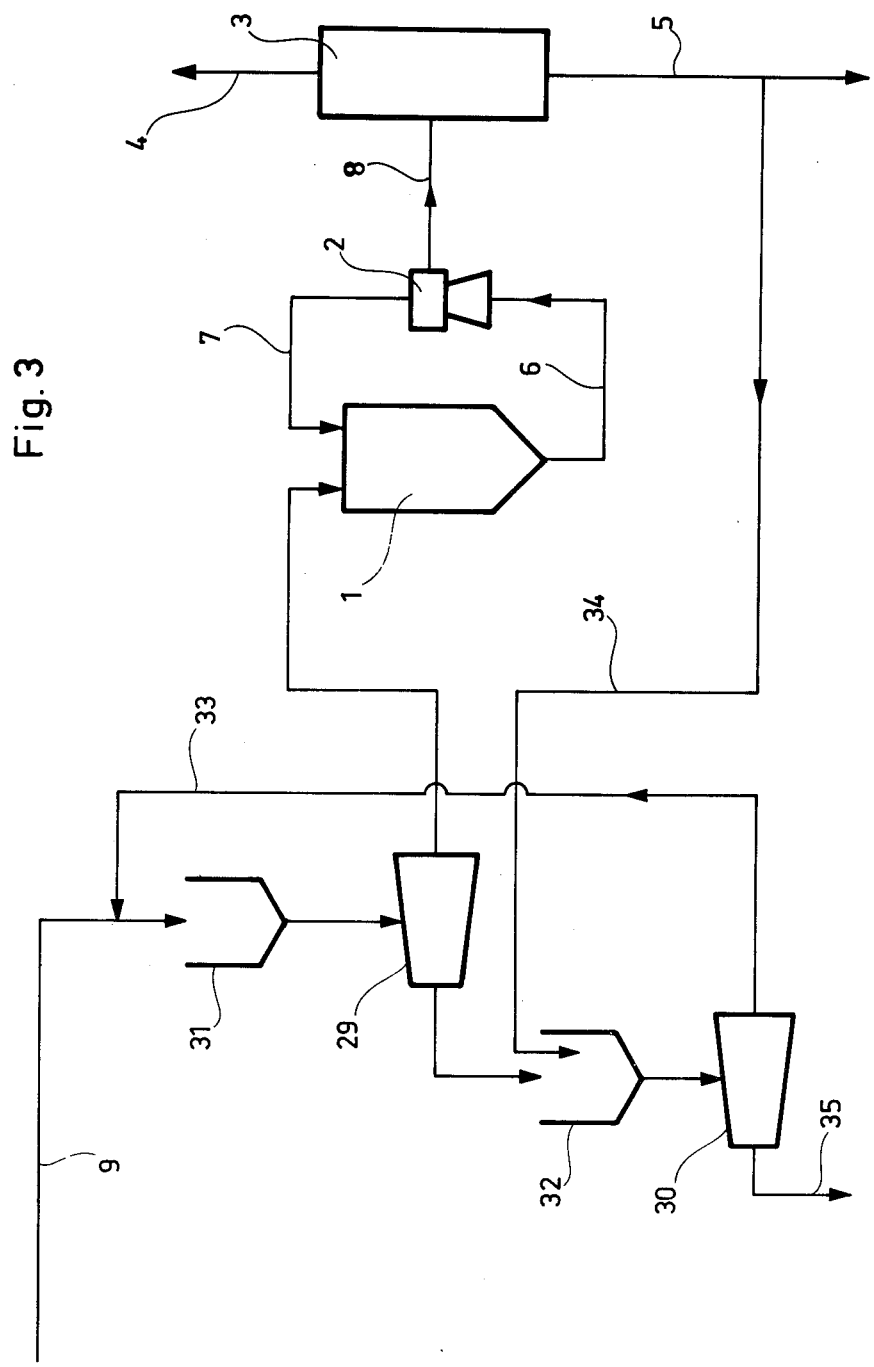
FIG. 3 shows a plant for the performance of the method according to the present invention, two centrifugal separators with horizontal rotor and a coaxial conveyor screw being used for recovery of substrate from flow, rich in solid substance being used.

The embodiment of said unit, which is shown in FIG. 3, consists, as mentioned above, of two centrifugal separators 29, 30 of the same type as that with reference number 26 in FIG. 2, and of two tanks 31, 32 provided with stirrers, not shown, the centrifugal separators and the tanks being coupled in series, as is obvious from the figure. A raw material flow is fed to tank 31 via pipe 9. Also a liquid flow coming from centrifugal separator 30 is fed to this tank through a pipe 33. A slop flow is fed, via a pipe 34 to tank 32, and relatively dry substance, rid of substrate, is discharged from the unit through a pipe 35.

We claim:

1. In the method of producing ethanol from a carbohydrate-containing substrate mixed with non-fermentable solids, said method including the steps of continuously separating said substrate and solids into a flow rich in said solids and a substrate flow free from said solids, passing said substrate flow to a fermenter to produce ethanol by fermentation of said carbohydrate in the presence of yeast, withdrawing continuously from the fermenter a discharge stream of fermentation liquor containing yeast and ethanol, centrifugally separating said discharge stream continuously into at least a yeast concentrate flow and a yeast-free ethanol-containing flow, recirculating said yeast concentrate flow to the fermenter, and continuously separating said yeast-free flow into an ethanol-enriched flow and a residual flow, the improvement which comprises contacting at least part of said residual flow with said flow rich in solids to form a mixture, continuously separating said mixture in a plurality of separators into solids from which remaining substrate has been substantially removed and a flow enriched in substrate, and returning said flow enriched in substrate to the fermenter.

2. The method of claim 1, in which said mixture is separated by at least one separating step with a sieve means while solids are retained against passage through the sieve means.

3. The method of claim 1, in which said mixture is separated by at least one centrifugal separator having a rotor journalled horizontally in bearings and a conveying screw arranged coaxially within the rotor for discharging said solids.

4. The method of claim 1, in which said contacting is effected by passing said residual flow and said flow rich in solids in countercurrent relation to each other through a plurality of separating means connected in series.

* * * * *